United States Patent [19]

Milnamow

[11] 3,967,624
[45] July 6, 1976

[54] DISPOSABLE DIAPER WITH TAB FASTENERS HAVING A PERFORATED COVER STRIP

[75] Inventor: John P. Milnamow, Barrington, Ill.

[73] Assignee: Johnson & Johnson, New Brunswick, N.J.

[22] Filed: Apr. 4, 1975

[21] Appl. No.: 565,295

[52] U.S. Cl............................... 128/287; 128/284
[51] Int. Cl.² .......................................... A61F 13/16
[58] Field of Search ................ 128/284, 287; 24/67

[56] References Cited
UNITED STATES PATENTS

| 3,620,217 | 11/1971 | Gellert | 128/284 |
| 3,642,001 | 2/1972 | Sabee | 128/287 |
| 3,646,937 | 3/1972 | Gellert | 128/287 |
| 3,750,669 | 8/1973 | De Luca | 128/287 |
| 3,776,234 | 12/1973 | Hoey | 128/287 |
| 3,875,621 | 4/1975 | Karami | 24/67 |

Primary Examiner—Aldrich F. Medbery

[57] ABSTRACT

A disposable diaper is provided with adhesive tab fasteners having the tacky surfaces thereof protected by perforated cover strips. The tacky areas presented through the perforations provide points of temporary attachment of the tab fastener free working ends to a diaper facing sheet so that the free working ends do not interfere with diaper manufacturing and packaging machinery.

6 Claims, 5 Drawing Figures

DISPOSABLE DIAPER WITH TAB FASTENERS HAVING A PERFORATED COVER STRIP

BACKGROUND OF THE INVENTION

This invention relates to disposable diapers. More particularly, this invention relates to disposable diapers adapted to be secured in place by adhesive tabs.

Disposable diapers provide substantial advantages in convenience over conventional diapers and commonly have a generally quadrilateral configuration with straight or curvilinear longitudinal edges. Disposable diapers comprise a moisture-impermeable backing sheet and a moisture-retaining layer anchored thereto, and are conveniently secured about an infant by means of adhesive tape tabs which are affixed to the diaper along a longitudinal edge thereof, thus eliminating the need for extraneous fasteners, such as pins. In order to protect the adhesive surfaces of the tape tabs, usually a cover strip having a release surface is applied over these adhesive surfaces for subsequent removal when the diaper is about to be used. However, such tabs usually project beyond the confines of the diaper to a considerable extent and interfere with the efficient manufacture and packaging of the diaper.

In an attempt to solve the foregoing problems, U.S. Pat. No. 3,776,234 to Hoey proposes to fold the tab over on itself at the diaper's edge and to adhesively attach a portion of the folded-over tab segment to an inwardly-folded margin of the diaper backing sheet in order to keep the tab flat against the diaper and thus from interfering with the manufacturing machinery and with the subsequent folding and packaging operations. This requires that the edge of the diaper backing sheet be folded over to present an attachment surface at the front or inside face of the diaper, and a relatively involved tab design is necessary for this purpose. Also, undesirable tearing of the diaper facing fabric may result if such a tab is inadvertently adhesively attached to the facing fabric of the diaper during manufacture.

U.S. Pat. No. 3,750,669 to DeLuca shows a fastening tape provided with an adhesive end portion which extends beyond a cover strip for the tape and which is attached to a diaper inner covering or facing. However, such an adhesive end portion, when attached to a fibrous, non-woven facing fabris is likely to tear the facing fabric upon separation therefrom.

U.S. Pat. No. 3,646,937 to Gellert shows a fastening tab which is provided with a release surface permanently bonded to the inside surface of the diaper; however, such an arrangement is disadvantageous because the release surface may be placed in contact with the infant's skin when the diaper is used and also because substantial areas of the backing sheet are placed in contact with the infant's tender skin.

Additionally, for ease of application of the diaper about an infant, a relatively long free end for the adhesive tab is desirable, yet the longer the free end the more severe are the manufacturing and packaging problems.

SUMMARY OF THE INVENTION

The present invention contemplates a disposable diaper provided with an improved adhesive tab fastener having a free working end held against a diaper facing and out of the way of manufacturing and packaging machinery. The disposable diaper embodying the present invention comprises a thin, moisture-impervious backing sheet, a moisture-retaining layer attached to the backing sheet and having a facing which forms a diaper inside surface for direction toward an infant when the diaper is worn by that infant, and a tab fastener means having a fixed end secured to the backing sheet on the outside surface of the diaper and at a marginal location thereof and a free working end provided with a layer of pressure-sensitive adhesive presenting a tacky surface which faces in the same direction as the inside surface of the diaper. A perforated cover strip is releasably held on the tacky surface and the free working end is folded over in abutment with the diaper inside surface and the tacky surface is in adhesive contact with the facing through the perforations in the cover strip. Preferably, the cover strip extends longitudinally beyond the tacky surface of the free end.

DESCRIPTION OF THE PREFERRED EMBODIMENTS

Figure 1:
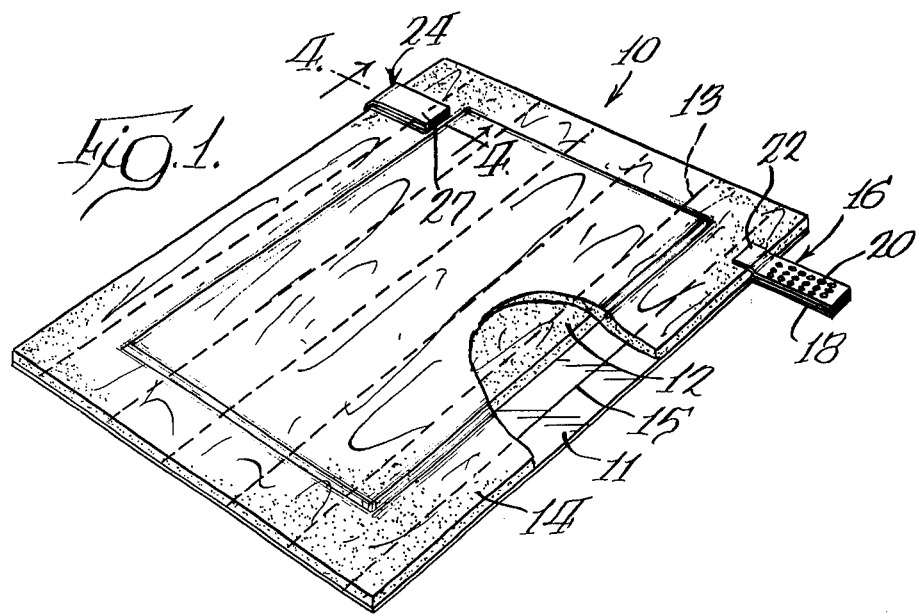
FIG. 1 is a perspective view of a disposable diaper embodying the present invention, parts of the diaper being broken away to show interior construction.
Figure 2:
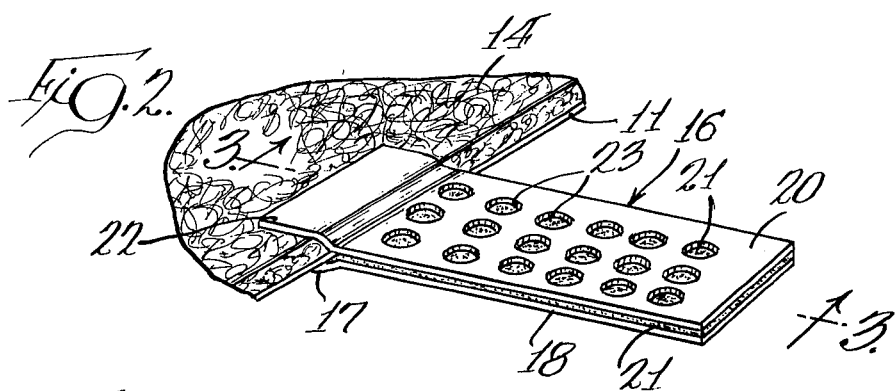
FIG. 2 is a fragmentary perspective view on an enlarged scale and showing a tab fastener of this invention.

Referring to FIGS. 1 and 2, disposable diaper 10, having a substantially quadrilateral configuration, is provided with moisture-impermeable backing sheet 11 which forms an outside surface for direction away from an infant and with an absorbent pad means 12 situated on backing sheet 11 and attached thereto by means of an adhesive bead such as bead 13, or the like. Moisture-pervious facing sheet 14, forming an inside surface for direction toward the infant, overlies absorbent pad 12 and is substantially coextensive with backing sheet 11. Facing sheet 14 is similarly attached to backing sheet 11 by a plurality of adhesive beads, such as bead 15, for example. Adhesive tab fastener 16 comprises fixed end 17 attached to the outer surface of backing sheet 11 at a marginal location of diaper 10 by adhesive layer 19 and free end 18 which extends beyond the longitudinal margin of diaper 10. Free end 18 can be longer than attached or fixed end 17 and is provided with a pressure-sensitive adhesive layer such as layer 21 which can be a continuation of adhesive layer 19.

Cover strip 20 covers pressure-sensitive adhesive layer 21 and extends longitudinally beyond the tacky surface of layer 21 to provide grippable end portion 22 which facilitates the removal of cover strip 20 so as to expose adhesive layer 21 when tab 16 is prepared for use. Cover strip 20 is provided with a plurality of perforations 23 (FIGS. 2 and 3) which expose portions of the tacky surface of adhesive layer 21.

Figure 3:
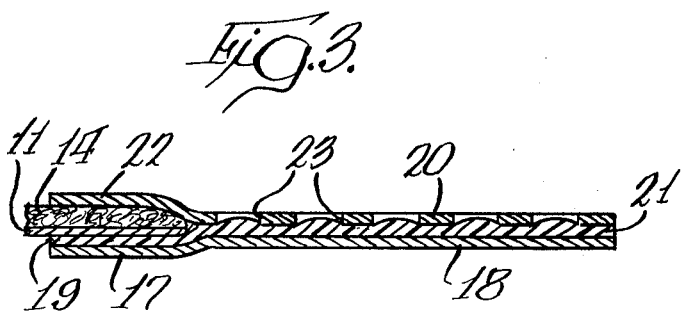
FIG. 3 is a fragmentary elevational view taken along plane 3—3 in FIG. 2.
Figure 4:
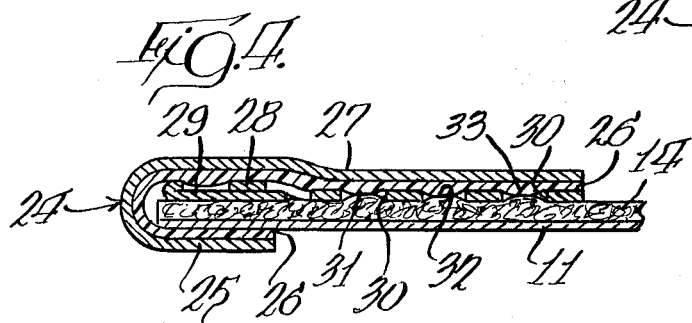
FIG. 4 is a fragmentary elevational view on an enlarged scale, taken along plane 4—4 in FIG. 1.

The rheological properties of adhesive layer 21 preferably are such that the pressure-sensitive adhesive protrudes slightly into perforations 23 as illustrated in FIG. 3. These protrusions provide separated anchor points at which the tacky surface of layer 21 can make adhesive contact with facing sheet 14 when the tab fastener is folded over the cover strip-protected free end thereof abutting facing sheet 14 as illustrated in FIGS. 1 and 4 by tab fastener 24. At the same time, these anchor points are sufficiently far apart from each other so as not to cause undesirable tearing of facing sheet 14 when tab fastener 16 is unfolded preparatory for use, yet the cumulative holding effort exerted at the anchor points is sufficient to hold tab fastener 16 in a folded-over configuration. In addition, to provide the desired anchor points it is advantageous to select a relatively thin perforated cover strip so that layer 21 is relatively thicker than cover strip 20. In this manner holding contact between the relatively soft and pliant facing sheet 14 and adhesive layer 21 can be readily established.

In the alternative, the size of perforations 23 can be selected so that the diameter of each perforation is at least about three times the thickness of cover strip 20.

The relative number of perforations in cover strip 20 is not overly critical and depends to a large extent on the extrudability of adhesive layer 21, the nature of facing sheet 14, and also on the resiliency of tab fastener 16 itself. Usually only a minor portion of cover strip 20 need be perforated to achieve the desired retention characteristics for free end 18 against facing sheet 14. In instances where it is desirable to minimize the number of perforations on a cover strip, the perforations can be situated near the distal portion of the free working end so as to maximize the benefit derivable from the hold-down leverage.

A tab fastener in the folded-over position and held against a diaper facing sheet is illustrated by tab fastener 24 in FIG. 4. Fixed end 25 thereof is secured to backing sheet 11 by means of adhesive layer 26 which is of the pressure-sensitive type and which is substantially coextensive with tab fastener 24. Free working end 27 is folded over against diaper facing sheet 14 and the tacky surface presented by adhesive layer 26 on the free working end 27 is protected by releasably held cover strip 28. Grippable end portion 29 of cover strip 28 extends beyond the tacky surface thereof and is retained in the resulting fold.

Cover strip 28 is also provided with perforations 30 and a portion of adhesive layer 26 is extruded therein to provide points of adhesive attachment 31, 32 and 33 which temporarily anchor tab free working end 27 to facing sheet 14 during diaper manufacture and storage. The perforated area of cover strip 28 is less than 50 percent of the total area of the tacky surface on free working end 27, and can be as low as about 5 to about 10 percent, depending on the aggressiveness of adhesive layer 26.

The adhesive tab suitable for the purposes of the present invention can be made from a wide variety of materials. Particularly preferred materials for this purpose are polyalkylene webs such as polyethylene sheet, polypropylene sheet, and the like.

The pressure-sensitive adhesive layers such as layers 21 and 26 are provided by applying a coating of a pressure-sensitive adhesive composition known in the art to the appropriate surfaces of respective tab free working end 18 or free working end 27. The applied adhesive shall have good tack, good cohesive strength, good resistance to moisture and good resistance to aging. Illustrative of such adhesive compositions are mixtures of natural or synthetic rubber, zinc oxide, and various resins, also latices of natural or synthetic rubber, or water dispersions of acrylic tacky polymers or copolymers, and the like. For enhanced extrudability into perforations 23 and 30, the pressure-sensitive adhesive can be foamed, i.e., prepared in a foamed state by incorporating therein during manufacture a blowing agent such as an emulsified halogenated hydrocarbon, or the like. Foamed adhesives are known in the art and are commercially available.

Cover strips 20 and 28 can be made from smooth plastic film having a relatively non-adhering surface, from paper coated with a silicone release compound, or from similar release materials which are perforated to the desired extent in any convenient manner.

Several different types of facing materials may be used for diaper facing sheet 14. For example, facing sheet 14 may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,663,348 to Liloia et al.

Facing sheet materials suitable for use in this invention can have fabric weights in the range of about 1 to 5 oz./yd.$^2$ and densities of less than 0.15 g./cc., generally in the range between 0.05 and 0.1 g./cc. The dry strength of the facing sheet for a fabric having a weight of about 1.5 oz./yd.$^2$ is at least 0.15 lbs./in. of width in the machine direction and at least 0.1 lbs./in. of width in the cross direction. Such fabrics have unusually good elongation, loft, softness, and drape characteristics in comparison to prior products incorporating any substantial amount of short fibers.

Facing sheet 14 may also be made of an apertured, nonwoven fabric which is formed, for example, in accordance with the teachings of commonly assigned U.S. Pat. Nos. 2,862,251; 3,081,514; and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, facing sheet 14 can be formed of a non-apertured material, such as a nonwoven isotropic web, or the like. In all of the aforementioned facing materials, the material should be relatively hydrophobic so as to retard wicking within the facing layer.

Highly moisture-absorbent fibrous pad or batt 12, which usually is substantially rectangular in shape but smaller than the facing sheet and the backing sheet, is centrally disposed between facing sheet 14 and backing sheet 11. Pad 12 is usually anchored to backing sheet 11 by means of an adhesive bead, heat sealing, or similar expedients. Pad 12 can be formed in accordance with the teachings of U.S. Pat. No. 3,612,055 to Mesek et al. If desired, a highly moisture-absorbent layer can be provided substantially coextensive with backing sheet 11 and facing sheet 14.

A suitable backing sheet material for the diapers embodying the present invention can be an opaque polyethylene web about 0.001 inch thick. Another suitable material for this purpose is a polyethylene terephthalate web having a thickness of about 0.0005 inch. Typical disposable diapers which can be fitted with tab-type adhesive fasteners described hereinabove are shown in U.S. Pat. No. 3,612,055 to Mesek et al. and in U.S. Pat. No. 3,683,916 to Mesek et al. Other suitable disposable diaper structures which can be improved by the present tab-type fasteners are shown in U.S. Pat. No. Re. 26,151 to Duncan et al.

Figure 5:
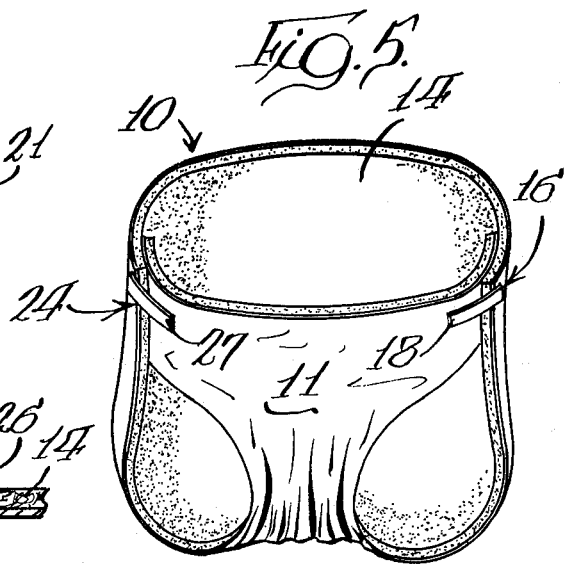
FIG. 5 is a perspective view showing the diaper of FIG. 1 in a configuration assumed when the diaper is applied about an infant.

In use, a diaper equipped with the adhesive fasteners of the present invention is applied to the infant by laying out the diaper on a suitable flat surface and placing the infant thereon so that the waist-underlying end of the diaper is that having the fastener means. The other end of the diaper then extends downwardly between the infant's legs. Next, the downwardly-extending end of the diaper is brought up between the infant's legs to a position contiguous with the front of the infant's waist. The diaper is thereafter secured to the infant by placing the corners of the waist portion of the abdomen-covering end as far around the infant's waist as they will go and by bringing the corners of the underlying end of the diaper into an overlapping relationship with the aforementioned corners so that the diaper snugly encircles the infant's waist and provides a custom fit. The adhesive fasteners are then prepared for use by pulling free working ends 18 and 27 away from their temporary engagement with facing sheet 14, grasping the exposed cover strip terminal portions such as portion 22 (FIG. 2) or portion 29 (FIG. 4) and pulling the cover strips away from the adhesive surface on the free ends of the adhesive tabs. The tabs are then used to secure the diaper in the desired position by simply urging the pressure-sensitive adhesive surfaces in contact with the adjacent outer surface of the diaper. The applied diaper assumes the configuration illustrated in FIG. 5.

The foregoing description and the drawing are illustrative but are not to be taken as limiting. Still other variations and modifications are possible without departing from the spirit and scope of the present invention.

I claim:

1. A disposable diaper which comprises a moisture-impermeable backing sheet forming a diaper outside surface for direction away from an infant when the diaper is worn by that infant, a moisture-retaining layer adhered to the backing sheet and having a facing which forms a diaper inside surface for direction toward the infant, tab fastener means having a fixed end secured to said diaper backing sheet and a free working end provided with a layer of pressure-sensitive adhesive presenting a tacky surface facing in the same direction as the diaper inside surface, a means for removably holding said free working end in contact with said inside surface comprising a perforated cover strip releasably held on said tacky surface; said free working end being folded over the edge of the diaper in abutment with said diaper inside surface and said tacky surface defining a limited adhesive contact with said facing at a plurality of attachment points through the perforations in said cover strip.

2. The disposable diaper in accordance with claim 1 wherein said pressure-sensitive adhesive protrudes into the perforations of said cover strip.

3. The disposable diaper in accordance with claim 1 wherein said layer of pressure-sensitive adhesive is thicker than said cover strip.

4. The disposable diaper in accordance with claim 1 wherein a minor portion of said cover strip is perforated.

5. The disposable diaper in accordance with claim 1 wherein the diameter of said perforations is at least about three times the thickness of said cover strip.

6. The disposable diaper in accordance with claim 1 wherein said layer of pressure-sensitive adhesive is foamed.

* * * * *